(12) United States Patent
Blum

(10) Patent No.: US 6,180,562 B1
(45) Date of Patent: Jan. 30, 2001

(54) COMPOSITIONS FOR PROTECTING PLANTS FROM FROST AND/OR FREEZE AND METHODS OF APPLICATION THEREOF

(75) Inventor: Ronald D. Blum, Roanoke, VA (US)

(73) Assignee: The Egg Factory, L.L.C., Roanoke, VA (US)

(*) Notice: Under 35 U.S.C. 154(b), the term of this patent shall be extended for 0 days.

(21) Appl. No.: 09/233,056

(22) Filed: Jan. 20, 1999

(51) Int. Cl.[7] ............................. A01N 25/04; A01N 25/28
(52) U.S. Cl. ................. 504/117; 504/363; 47/2; 71/27; 514/772; 514/773; 514/944; 514/975
(58) Field of Search ................... 504/363, 117; 47/2; 71/27; 514/772, 773, 944, 975

(56) References Cited

U.S. PATENT DOCUMENTS

| | | | |
|---|---|---|---|
| 2,579,451 | 12/1951 | Polson | 18/54 |
| 2,812,317 | 11/1957 | Barrett | 260/88.7 |
| 2,861,059 | 11/1958 | Mowry et al. | 260/85.5 |
| 3,200,102 | 8/1965 | Kleiner | 260/88.7 |
| 3,563,461 | 2/1971 | Cole | 239/9 |
| 3,584,412 | 6/1971 | Palmer | 47/2 |
| 3,615,972 | * 10/1971 | Morehouse et al. | 156/79 |
| 3,709,842 | 1/1973 | Stoy | 260/2.5 R |
| 3,864,323 | 2/1975 | Stoy | 260/88.7 R |
| 3,897,382 | 7/1975 | Stoy et al. | 260/29.6 AN |
| 4,161,084 | 7/1979 | Arny et al. | 47/2 |
| 4,183,884 | 1/1980 | Wichterle et al. | 264/41 |
| 4,352,458 | 10/1982 | Masel | 239/77 |
| 4,363,760 | 12/1982 | Cioca | 260/123.7 |
| 4,419,288 | 12/1983 | Cioca | 260/123.7 |
| 4,963,656 | 10/1990 | Mitani | 530/353 |
| 5,052,618 | 10/1991 | Carlon et al. | 239/77 |
| 5,082,177 | 1/1992 | Hill et al. | 239/77 |
| 5,185,024 | 2/1993 | Siemer et al. | 504/116 |
| 5,285,769 | 2/1994 | Wojcicki | 126/59.5 |
| 5,653,054 | 8/1997 | Savignano et al. | 47/2 |
| 5,668,082 | 9/1997 | Miller et al. | 504/116 |
| 6,057,266 | 5/2000 | Colvin et al. | 504/100 |

\* cited by examiner

*Primary Examiner*—S. Mark Clardy
(74) *Attorney, Agent, or Firm*—Kenyon & Kenyon

(57) ABSTRACT

Compositions and methods of applying the compositions to plants are disclosed. The compositions include a polymer component that releases heat over a range of dropping ambient temperatures beginning at about 32° F. By exhibiting a broad freezing temperature transition range, the compositions, when applied to plants, effectively reduce the threshold temperature at which substantial frost and/or freeze damage to plants will occur.

29 Claims, 1 Drawing Sheet

COMPOSITIONS FOR PROTECTING PLANTS FROM FROST AND/OR FREEZE AND METHODS OF APPLICATION THEREOF

FIELD OF THE INVENTION

This invention relates generally to compositions suitable for application to plants and to methods of applying the compositions to plants. In particular, the invention relates to polymer compositions for application to the surfaces of plants for protecting the plants from damage caused by frost and/or freeze.

BACKGROUND OF THE INVENTION

Frost and/or freeze can cause extensive damage to agricultural products. A significant factor in frost formation is radiative cooling from the earth's surface and crops growing thereon. Such radiative cooling results in heat loss to the atmosphere, and is particularly prevalent on windless clear nights. Hence, several methods have been used to protect plants from damage caused by frost and/or freeze.

For example, an early preventative measure involved the use of smudge pots in orchards. The smudge pot operated by burning oil in a container. Heat was thus produced to raise the temperature in the orchard to above dangerous levels. The smoke generated by the burning also provided a blanket of insulation that helped to retain the heat in the orchard.

Another conventional technique is to spray water over the orchard or crops. This increases the dew point of the air which helps the air to trap and hold the earth's radiant heat. Also, condensation of the water vapor on the fruit releases energy (i.e., the heat of fusion), thus raising the temperature of the fruit.

Other methods of forming insulative fog and/or mist layers are also known. For example, U.S. Pat. No. 5,052,618 to Carlon et al. discloses a method of protecting plants from frost by using a jet engine to generate an aerosol of a first liquid microencapsulated in a second liquid. The aerosol is dispersed in a mist about the plants to be protected from frost. The mist acts as a protective radiation barrier for the plants. U.S. Pat. No. 4,352,458 to Masel discloses a device for generating and transporting over substantial distances a jet of hot combustion gases having entrained therein condensed water. The generated jet of gases and entrained condensed water provides a vapor mist, and the device is movable from one location to another in a manner so as to maintain a cloud of vapor in a desired orientation with respect to growing crops and over a desired amount of time.

Yet another technique involves using wind machines to generate a wind stream which forces cold air up and warm air down into the orchard. Such wind machines can also be used in conjunction with means for introducing a moisture mist into the generated wind stream to further protect crops from frosting during cold nights.

Other methods include, for example, use of a pulse-jet engine as described in U.S. Pat. No. 5,285,769 to Wojcicki that generates individual bursts of pulses of heat over a pulse cyclic period. The combustion products are in the form of a hot jet which is exhausted to the orchard to raise the temperature and prevent or reduce the risk of freeze damage to fruit trees or similar crops.

Yet another technique for protecting crops against frost damage is direct water sprinkling of the crops. In this method, the radiative heat loses are partially compensated for by the latent heat produced by freezing of the water drops. The Masel patent, discussed above, notes that this technique suffers from the disadvantage that significant amounts of ice, having a conductivity four times that of water, are formed on the crops, for example, on the leaves of fruit trees. Therefore, the ice thus formed enhances the cooling of the leaves. Furthermore, the weight of the ice can damage the plant.

Water has also been combined with other components to form freeze preventative and/or protective compositions for direct application to plant surfaces. Such compositions for direct application to plants have mainly involved the use of freezing point depressants, such as monohydric alcohols, small chain dihydroxy and polyhydroxy alcohols, such as propylene glycol, polyalkyl glycols, and so forth, and other agents such as cross-linked polyacrylic acid.

For example, U.S. Pat. No. 5,653,054 to Savignano et al. discloses a composition for preventing or retarding frost formation on grass or leafy plants comprising a mixture of water, a water-soluble freezing point depressant such as propylene glycol, and a water dispersible thickening agent such as a cross-linked polyacrylic acid polymer. The composition is applied by spraying and, preferably, just prior to expected frost onset. The composition protects plants by lowering of the freezing point of moisture that condenses or collects overnight on plant surfaces treated with the composition.

U.S. Pat. No. 5,668,082 to Miller et al. discloses a "sticker" composition and/or "sticker/spreader" adjuvant combined with active materials used in the agricultural and horticultural industry. The composition comprises a low molecular weight polyolefin hydrocarbon resin and an active material such as insecticides, herbicides, fungicides, rodenticides, nutrients, plant growth regulators, pheromones and defoliants. The patent broadly discloses that the invention can be extended with beneficial results to the retention and dispersion of various protective coatings on numerous fruit and vegetable varieties for protection from excessive heat, cold or sun exposure. However, the patent discloses no compositions specifically designed for protection of plants from frost and/or freeze.

U.S. Pat. No. 5,185,024 to Siemer et al. discloses application of cross-linked hydrated polyacrylamide and poly (ammonium) acrylate hydrogels to agricultural soils or crops by spraying. The hydrogels are described as typically rigid and insoluble and may include such additives as surfactants, plant micronutrients or macronutrients, pesticides, plant growth regulators, freezing point depressants, microbes and colorants. The patent discloses that hydrogels can be used as soil amendments and for the treatment of crop foliage. For example, use of hydrogels can substantially reduce the use of irrigation water by retention of moisture in the soil or around crop roots. When surfaces of living or cut plants are coated with hydrogels, transpiration of water through the leaves is limited, thus prolonging survival of living leaves in plants stressed for water, and prolonging the period of pleasing appearance of cut plants or flowers. The patent also discloses that hydrogels have been applied to the surface of crop plants to protect the foliage from frost damage by taking advantage of the high latent heat capacity of water to protect the plants. The patent discloses specific examples of spraying the hydrogels onto turf subjected to hot and dry weather conditions and of spraying the hydrogels onto pinto bean seeds or on the surface of the sand after planting the beans.

ADVANTAGES OF THE INVENTION

It is an advantage of the invention to provide a composition for application to plants to protect plants from damage caused by frost and/or freeze.

It is another advantage of the invention to provide a method for application to plants of a composition to protect plants from damage caused by frost and/or freeze.

SUMMARY OF THE INVENTION

These and other advantages of the present invention that will become apparent from the following detailed description of the invention are achieved, in one embodiment, by providing a composition comprising a polymer that, when applied to at least a portion of a surface of a plant, releases heat over a range of dropping ambient temperatures beginning at about 32° F. In another embodiment of the present invention, there is provided a method of applying a composition to a plant comprising coating at least a portion of a surface of said plant with a composition comprising a polymer that releases heat over a range of dropping ambient temperatures beginning at about 32° F. In a preferred embodiment of the present invention, the range of dropping ambient temperatures is from at least about 32° F. to about 27° F. In a particularly preferred embodiment of the present invention, the range of dropping ambient temperatures is from at least about 32° F. to about 22° F. In a preferred embodiment of the present invention, the polymer is a hydrated polymer gel. In a particularly preferred embodiment of the present invention, the hydrated polymer gel comprises a substantially uncrosslinked polymer. In another preferred embodiment of the present invention, the composition comprises an aqueous solution of the hydrated polymer gel. In yet another preferred embodiment of the present invention, the composition comprises water droplets coated with said hydrated polymer gel. In still another preferred embodiment of the present invention, the composition comprises a hydrated polymer gel in the form of a foam. In a particularly preferred embodiment of the present invention, the hydrated polymer gel foam comprises air bubbles having a diameter in the range of from about 100 to about 1000 microns. In a particularly preferred embodiment of the present invention, the hydrated polymer gel is hydrated copolymer gel. In another particularly preferred embodiment of the present invention, the hydrated polymer gel is formed by hydrolyzing a polymer. In an another particularly preferred embodiment of the present invention, the hydrated polymer gel is hydrolyzed polyacrylonitrile. In another particularly preferred embodiment of the present invention, the hydrated polymer gel is a hydrolyzed fibrous protein. In an even more preferred embodiment of the present invention, the hydrolyzed fibrous protein comprises amino acid and acrylamide moieties. In yet another preferred embodiment of the present invention, the hydrolyzed fibrous protein is selected from the group consisting of hydrolyzed fibronectin and hydrolyzed elastin. In another preferred embodiment of the present invention, the hydrolyzed polyacrylonitrile comprises acrylic acid and acrylamide moieties. In a particularly preferred embodiment of the present invention, the hydrolyzed polyacrylonitrile is uncrosslinked. In a preferred embodiment of the present invention, the composition is applied to the plant by spraying. In a particularly preferred embodiment of the present invention, a composition comprising water droplets coated with a hydrated polymer gel is applied and then a composition comprising an aqueous solution of said hydrated polymer gel is applied. In a preferred embodiment of the present invention, the composition further comprises one or more components selected from the group consisting of micronutrients, macronutrients, pesticides, insecticides, herbicides, rodenticides, fungicides, biocides, plant growth regulators, fertilizers, microbes, soil additives, adhesion promoting-agents, surfactants and freezing point modifiers. In particularly preferred embodiment of the present invention, the freezing point modifier is a freezing point depressant.

DETAILED DESCRIPTION OF THE INVENTION

Figure 1:
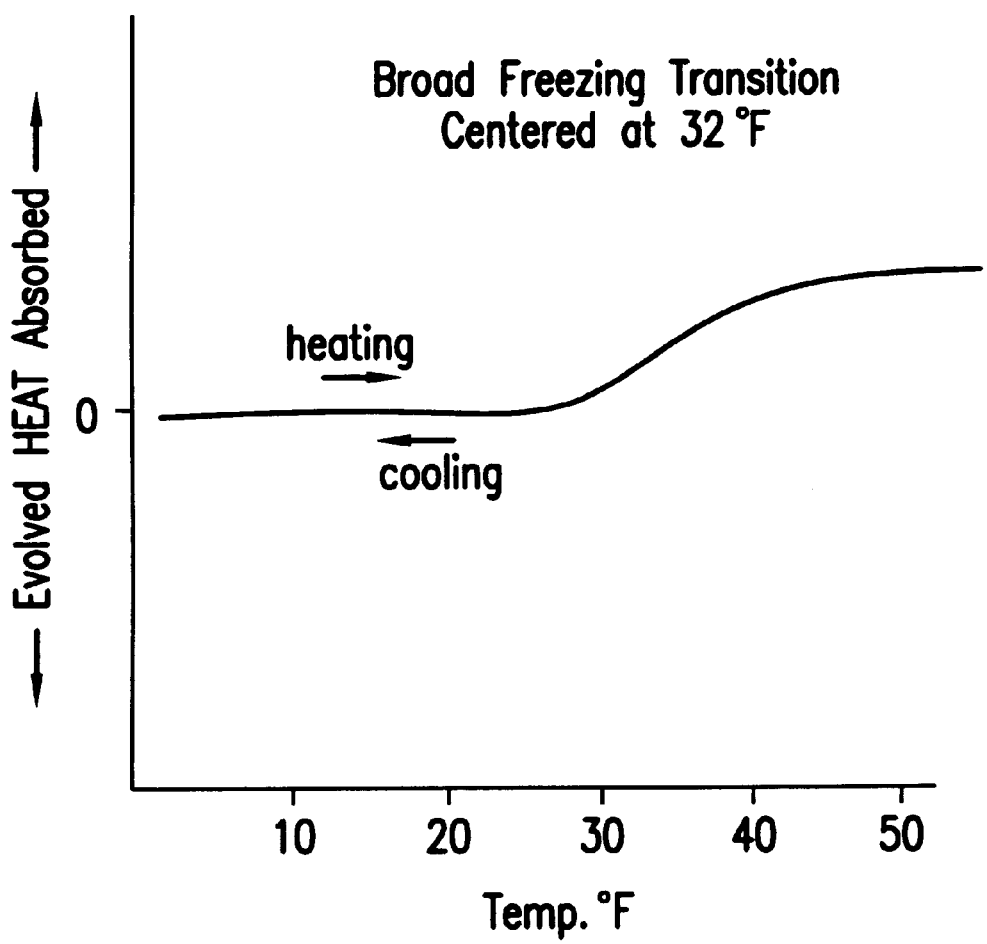
FIG. 1 shows a broad freezing transition for a polymer in accordance with the present invention.

The compositions of the present invention, when applied to at least a portion of a surface of a plant, have utility in protecting the plant from frost and/or freeze by releasing heat over a range of dropping ambient temperatures beginning at about 32° F. Thus, the compositions of the present invention effectively reduce the threshold temperature at which substantial frost and/or freeze damage to plants will occur.

While not being bound by any particular theory of the invention, is believed that heat is released over a temperature range because the polymers in the compositions of the present invention exhibit a broad freezing transition range beginning at about 32°, preferably in a range of from at least about 32° F. to about 27° F. or lower, and more preferably in a range of from at least about 32° F. to about 22° F. or below. This broad freezing transition enables the polymers to release their latent heat of fusion over a broad temperature range.

It is believed that in a particular polymer in accordance with the present invention, there can exist water molecules associated therewith by several different mechanisms. Depending on the particular mechanism of association with the polymer, different water molecules associated with a particular polymer may exhibit different freezing points. Thus, as the temperature falls within the range of these different freezing points, the latent heat of fusion is released over this range.

For example, it is believed that some of the water molecules may be associated with the polymer such that their freezing point is close to 32° F., hence these water molecules will release their latent heat of fusion at about 32° F. It is believed that such water molecules that have a freezing point of about 32° F. may be more loosely associated with the polymer. In contrast, it is believed that some water molecules in the same polymer may be directly hydrogen bonded to moieties (such as, for example, hydroxy and amino groups) within the polymer chain and may exhibit significantly lower freezing points, such as 27° F. or lower. Thus, it is believed that water molecules that are associated with moieties closer to the backbone of the polymer chain will exhibit a lower freezing point than water molecules that are further from the backbone of the polymer chain.

In a simplified sense, presented only for purposes of illustration, the polymer may be visualized as having water associated therewith in layers that, depending on their distance from the polymer backbone, will exhibit different freezing points. Hence, those water molecules closest to the polymeric backbone will have the lowest freezing point and those further from the polymer backbone will have the higher freezing points which will also be closest to the normal 32° F. freezing point of water.

It has been discovered that certain polymers in accordance with the present invention exhibit a broader freezing point transition range that renders such polymers optimally suited for releasing latent heat of fusion over this range, thus providing protection to the plant over a broader range of ambient temperature conditions. Greater protection is provided to plants when polymers having the broadest freezing point range are employed. This is exemplified by comparing the polymers of the present invention having a broad freezing point transition to water not associated with any polymeric material. Thus, if water were applied to the surface of the plant, it would release its latent heat at a temperature of 32° F. and thus would provide little protection to the plant as the ambient temperature dropped below 32° F. Furthermore, it is difficult to form a uniform layer of water on the surface of the plants. Moreover, ice has a much higher thermal conductivity than water in the liquid state so that any heat that is released and retained by the plant is, upon freezing, much more readily lost by conduction through the ice layer.

The polymers in accordance with the present invention will, however, release heat over a temperature range and will also provide an insulative layer that helps retain the heat within the plant structure, thus affording greater protection to the plant. It is believed that the broadest temperature range over which the latent heat of fusion is released will be found in those polymers in accordance with the present invention that have regions with a higher number density of hydrophilic and hydrogen-bonding groups interspersed among regions having a comparatively lower number density of hydrophilic and hydrogen-bonding groups.

In the case of a hydrolyzed polyacrylonitrile in accordance with the present invention, which forms an uncrosslinked polyacrylamide-polyacrylic acid gel, these hydrophilic and hydrogen-bonding groups will typically comprise the hydroxyl groups in the acrylic acid moieties and the amino groups in the acrylamide moieties. It is believed that the water associated with polymers having regions with a higher number density of hydroxyl groups interspersed amongst regions having a comparatively lower number density of hydroxyl groups is less likely to crystallize upon encountering ambient temperature conditions at which the latent heat of fusion of the water will be released.

Thus, it is believed that the polymers in accordance with the present invention, in a preferred embodiment, release latent heat of fusion over a broad temperature range when the water associated with the polymer undergoes a phase transition that results in an amorphous rather than crystalline structure. Crystalline domains, if formed, tend to be small, typically less than about 2000 Å, and disordered within an amorphous matrix. Thus, whereas water not associated with the polymer would exhibit a distinct phase change to a crystalline state at a specific temperature and would release heat only at this temperature, the water associated with the polymers in accordance with the present invention exhibits a phase change to a comparatively less crystalline and more amorphous state and over a temperature range in contrast to a specific temperature and also release heat over this temperature range.

It is believed that much of the heat that is released from such polymers in accordance with the present invention over the freezing point transition range is transferred to the plant body which is thereby protected from freezing. The coating layer may also insulate the plant, so that the transferred heat is more effectively retained within the plant.

Additionally, it is believed that the compositions of the present invention may also have the ability to depress the freezing point of water that might condense and/or collect on the plant surfaces subsequent to application of the composition to the plant.

Regardless of the actual mechanism of their operation, the compositions of the present invention are applied such that at least a portion of the plant surface is coated with the composition. The invention is not limited to application of the compositions to any particular type of plant or to any particular stage of development of the plant or to any particular portion of the plant. Thus, the compositions of the present invention may be applied to any plant, at any stage in its development, and to any portion thereof that might benefit from protection from frost and/or freeze. Such plants include, for example, any conventional agricultural crop that may be intended for human and/or animal consumption such as fruits, vegetables, grass, hay, and so forth, or to plants grown for other purposes including, but not limited to, ornamentation, including flowers and shrubs, forestation development, erosion protection, diverse industrial applications, and so forth.

The compositions of the present invention may be applied to plants that are immature, e.g., sprouts, seedlings, and so forth, as well as to more mature plants, e.g., those that are budding, fruit-bearing, foliage-bearing, and so forth.

Furthermore, the compositions of the present invention are not limited to application to growing plants. Thus, the compositions of the present invention may be applied to plants, or any portion thereof, that have been severed from the land, but that are still subject to environmental conditions that may result in frost and/or freeze damage thereto.

The compositions of the present invention may be applied to the plants in any manner that results in at least a portion of the plant surface being coated with the compositions. Thus, the invention is not limited to any particular mode of application. Hence any conventional method used to contact plants with liquids, semi-liquids, gels, solids, and so forth, may be employed. For example, the compositions of the present invention may be applied by spraying, for example, via nozzles or sprinkling systems, by broadcasting, dousing, soaking, and so forth. A preferred method of application of the compositions of the present invention is spraying. Any conventional spraying method or apparatus may be employed for this purpose.

The compositions of the present invention may be applied in the form of an aqueous solution. For example, in the case of a hydrated polymer gel, an aqueous solution of the hydrated polymer gel may be applied.

The compositions of the present invention may also be applied in the form of water droplets coated with a polymer (e.g., microcapsules) in accordance with the present invention. Preferably, the polymer coating the water droplets is a hydrated polymer gel. Such coated water droplets may be formed by any conventional method including microencapsulation techniques in which water droplets are coated with a layer of a polymer in accordance with the present invention. Microencapsulation is a technique for providing a thin coating on typically micron-sized particles, that may be liquid, solid, semi-solid, and so forth. A typical microencapsulation technique that may be used to produce coated water droplets in accordance with the present invention involves forming a mist of water droplets using an atomizing spray gun or an ultrasonic nozzle, then intersecting the stream of droplets with an orthogonal stream of droplets of the hydrated gel solution, as described by Palmer, U.S. Pat. No. 3,584,412, which is incorporated herein by reference.

Other methods of forming water droplets coated with a polymer in accordance with the present invention include, for example, forming a suspension of water with a nonaqueous solution (e.g. a suspension) of the hydrated gel, then spraying the suspension through a fine nozzle. A volatile polar liquid immiscible with water is required to form the suspension which develops a micellar structure when water is added to the solution (or suspension) of the hydrated gel in this liquid. Suitable polar liquids useful in this method include, for example, acetonitrile, 1-hexanol and isopropyl ether. However, upon spraying, the polar liquid is evaporated and can result in environmental harm.

Prior to application of the coating layer, the size of the water droplets to be coated with a polymer in accordance with the present invention may range from about 0.1 mm to about 1.0 mm, preferably, from about 0.3 to about 1.0 mm. The thickness of the polymer layer coating the water droplets may range from about 100 microns to about 500 microns, preferably, from about 300 microns to about 500 microns.

When applying coated water droplets to plants in accordance with the present invention, it is preferable to initially apply the coated water droplets then to apply an aqueous solution of the polymer. However, this sequence is merely preferred and may be reversed. By repeated application of coated water droplets and aqueous solution of the polymers, multiple layers can be achieved. One advantage of applying the composition of the present invention in the form of coated water droplets is that it allows a plant to be coated with an effectively greater reservoir of water than would be the case if only the aqueous solution were applied to the plant. Moreover, it may be undesirable to include too much water in a hydrated polymer gel since the gel may become fragile and may lose its desired behavior of freezing over a wide temperature range. Thus, the additional water provided by the water droplets obviates the problem of using a polymer that is so hydrated that its efficacy is substantially reduced. Without being held to any particular theory of operation, it is believed that hydrogen bonding of the water encapsulated within the polymeric coating layer stabilizes the encapsulated water droplet, slows down evaporation of the water and, allows the coating to retain its structural integrity through several days of use. Preferred polymers used to coat the water droplets in accordance with the present invention are the polyacrylic acid and polyamino acid gels that are described below.

The composition of the present invention may also be applied in the form of a foam. When applied as a foam, the polymer is used to entrap air bubbles to form a stable foam. It is believed that the inner and outer surfaces of the polymer undergo cross-linking through hydrogen bond formation, adding structural integrity to the foam. The foam may be formed by any conventional means, e.g., by creating air bubbles of controlled sized in a solution of the polymer gel which leads to a stable suspension of air bubbles coated with the gel. The foam thus formed may be applied by any of the methods discussed above. A preferred method of applying the foam is by spraying. The foam may be substantially transparent or reflective, depending on the size of the air bubbles enclosed by the polymer, and the water content of the gel. A gel having a water content in the range of from about 50% to about 90% is preferred. In general, large pore foam is preferred. Therefore, it is preferred that the diameter of the air bubbles in the foam be in the range of from about 10 to about 100 microns. A foam having air bubbles in the 10 to about 100 micron diameter range will reflect about 3% of the visible radiation incident upon it, provided that the polymer gel has a water content of about 70 wt. %, and the dry polymer has a refractive index about 1.50. The polymers in accordance with the present invention that are most suitable for foam formation are those that have a refractive index of the dry polymer preferably in the range of from about 1.40 to about 1.60.

The foams in accordance with the present invention can be used in conjunction with the aqueous solution and coated water droplet forms of the composition. Thus, for example, a first layer of coated water droplets may be applied to a plant surface, followed by a layer of the aqueous solution, followed by a foam layer. It is to be understood that this sequence is merely exemplary and other sequences may be used, and multiple layers may thus be formed.

The compositions of the present invention, when applied to at least a portion of a plant surface, preferably will provide frost protection for several days before losing some efficacy due to dehydration caused by evaporation of the water molecules associated with the polymers. Even upon evaporative loss of the water molecules, it is believed that the polymers of the present invention maintain their integrity as coatings by reorganizing their structure. Thus, the polymers preferably continue to provide insulative protection to the plant, despite gradually losing their ability to release heat upon encountering freezing conditions. Moreover, the polymers of the present invention can regenerate their ability to release heat upon encountering freezing conditions by being remoisturized, for example, by exposure to humid conditions, particularly rain, or if the plant is irrigated.

The compositions of the present invention are also advantageous in that the polymer component of the composition enhances the ability of the composition to adhere to the surface of the plant and to form relatively thin and uniform coatings on the surface of the plant. Thus, the compositions of the present invention provide optimal frost and/or freeze protection when the polymer and water associated therewith is applied to the plant in an amount to provide a coating comprising from about 0.5% to about 3% of the weight of the plant body to be coated. In a typical application, the gel material will comprise about 30% of the weight of the coating. Thus, in a preferred coating application, the gel material will preferably comprise from about 0.15% to about 0.9% of the weight of the plant body to be coated. In a coating application where the coating comprises 1% of the weight of the plant body, the gel material will comprise 0.3% of the weight of the plant body.

The preferred weight percentages can be obtained, typically, when the composition of the present invention forms a coating having a thickness in the range of from about 200 microns to about 1000 microns. It is to be understood that the weight and thickness ranges are merely exemplary. Thus, application of a greater weight of coating material relative to the weight of the plant body, hence a greater coating thickness, will provide greater protection against frost and/or freeze. For example, a coating that is applied at a 2% level relative to the weight of the plant body will release approximately twice as much heat as would a coating applied at a 1% level. Thus, greater levels of heat will be released and a greater level of protection will be afforded when the higher coating levels are used. Extra protection may be desired, for example, when a longer spell of freezing conditions is expected or when protection is desired over a larger temperature range of the ambient air.

Upon encountering freezing conditions, the compositions of the present invention will typically release about 40 to about 70 calories per gram. However, it is to be appreciated that the amount of heat released will depend on the particular polymer used and its level of hydration, among other factors.

The compositions of the present invention may also include other components in addition to the polymer. For example, the compositions may include one or more components such as micronutrients, macronutrients, pesticides, insecticides, herbicides, rodenticides, fungicides, biocides, plant growth regulators, fertilizers, microbes, plant growth regulators, soil additives, adhesion promoting-agents, surfactants, freezing point modifiers, and so forth. Thus, the compositions of the present invention can include virtually any additional component(s) that is/are conventionally used in the treatment of plants. In addition, the compositions can include components used for the treatment of soil, such a fertilizers, soil amendments, and so forth. Thus, the compositions of the present invention can function as carriers for such additional components that may be dispersed, dissolved or otherwise incorporated within the compositions or any distinct phase or portion of such compositions.

Furthermore, the compositions of the present invention may include other additives that enhance and/or alter the properties of the coating per se without deleteriously affecting the broad freezing range of such compositions. For example, freezing point modifiers, preferably freezing point depressants, can be added to the compositions of the present invention to further reduce the freezing temperature of the compositions of the present invention. Such freezing point depressants include, for example, monohydric alcohols, small chain dihydroxy and polyhydroxy alcohols such as ethylene glycol and propylene glycol, among others, and polyalkylene glycols such as polyethylene glycol and polypropylene glycol, among others.

Surfactants (also known in the art as spreaders, film extenders and wetting agents) such as nonionic, cationic, anionic and amphoteric surfactants can also be included within the compositions of the present invention. Ionic surfactants, for example, when added to the compositions of the present invention, may promote cross-linking of the polymers upon application to a plant surface and hence promote a more stable coating layer. On the other hand, nonionic surfactants, when added to the compositions of the present invention, may help to prevent clumping of the polymer thus facilitating a more uniform coating layer. Polyhydric alcohols can be added to an aqueous solution of the polymer gels of the present invention in order to reduce the surface energy of the hydrated gel particles. Examples of polyhydric alcohols that can be used include, for example, small chain dihydroxy and polyhydroxy alcohols such as ethylene glycol and propylene glycol, among others, and polyalkylene glycols including polyethylene glycol and polypropylene glycol, among others. By thus reducing the surface energy of the hydrated gel particles, surface wetting and coverage may be increased.

Surfactants may also be used to increase the resistance of a component added to the compositions of the present invention from being removed by rain, dew or irrigation. Anionic surfactants also helpful in preventing such additives from being readily absorbed through plant cuticles, and are thus used when it is important for the additive to remain on the outer surface of the plant. Non-ionic surfactants, on the other hand, are useful when it is desired to increase the transport of such an additive through plant cuticles, and are therefore recommended for use with systemic herbicides, nutrients and the like.

The compositions of the present invention may also include one or more substances that improve the adhesion of the composition, or any component within the composition, to a surface of a plant. Such adhesion-promoting substances are known in the art at "stickers". Stickers, for example, can improve the adhesion of finely-divided solids or other water-soluble or -insoluble materials to plant surfaces. Thus, stickers can improve resistance of a plant treatment material provided as a coating to a plant surface to the effects of time, wind, water, mechanical or chemical action. For example, a sticker can improve the adhesion of a pesticide added to the compositions of the present invention against wash-off due to rainfall, heavy dew or irrigation, and also help prevent pesticide loss from wind or leaf abrasion. It is to be understood that, when added to the compositions of the present invention, stickers will improve the adhesion properties that are inherently present in the compositions of the present invention by virtue of the polymer component therein.

The compositions of the present invention comprise polymers that release heat over a range of dropping ambient temperatures beginning at about 32° F. One example of a polymer in accordance with the present invention that releases heat over a range of ambient temperatures beginning at about 32° F. is a hydrolyzed polyacrylonitrile. Upon hydrolysis of polyacrylonitrile by a strong base, such as an aqueous solution of sodium hydroxide, it is believed that a copolymer of acrylamide and acrylic acid is formed. This copolymer is a water-soluble, uncross-linked polyacrylamide-acrylic acid gel that is believed to be held together by hydrogen bonds. It is believed that the polymer gel has a hydration shell surrounding the polymer chain and that the hydration shell helps to keep the polymer in aqueous solution. A slightly acidic pH range of the aqueous solution facilitates maintaining the polymer in aqueous solution. Preferably, a pH of the aqueous solution of from about 5 to about 7 is maintained in order to keep the polymer in solution. The polyacrylamide-acrylic acid gel thus formed is hydrated to a water content preferably in the range of from about 70 wt to about 90 wt %. As discussed above, gels having a higher water content may become fragile and lose their desired freezing behavior occurring over a wide temperature range.

It is particularly preferred that the polymers in accordance with the present invention be substantially uncrosslinked, or have a relatively low amount of crosslinking. It has been found that highly crosslinked polymers will release less heat upon encountering ambient temperature conditions at which frost and/or freeze protection is desired. It is possible that such highly crosslinked polymers release less heat and are thus less preferred for the purposes of the present invention because such polymers have less ability to become associated with water molecules in the manner which is believed to result in the freezing point transition range that is most desired for the purposes of the present invention. While uncrosslinked polymers exhibiting the broad freezing point transition discussed hereinabove are particularly preferred, polymers that have some degree of crosslinking are also useful for the present invention where such crosslinked polymers also exhibit the broad freezing point transition. Thus, crosslinked polymers that release heat over a range of dropping ambient temperature beginning at about 32° F. are also useful in the present invention.

The hydrolyzed polyacrylonitriles that may be used in the compositions of the present invention can be prepared by known methods, including both acid and alkaline hydrolysis of polyacrylonitriles to form a polymer containing acrylamide and acrylic acid moieties. A preferred method involves hydrolyzing polyacrylonitrile by a strong base such as an aqueous solution of sodium hydroxide to produce a substantially uncrosslinked and water-soluble polyacrylamide-acrylic acid gel that is believed to be held together by hydrogen bonds. While, as discussed above, the alkaline hydrolysis product will contain both acrylamide and acrylic acid moieties, it may also contain some unhydrolyzed acrylonitrile moieties. U.S. Pat. No. 2,812,317, incorporated herein by reference, discloses alkaline hydrolysis of polyacrylonitrile to produce a polymer in which from about 40% to about 80% of the nitrile groups have been hydrolyzed to carboxyl groups. U.S. Pat. No. 2,861,059, incorporated herein by reference, discloses alkaline hydrolysis of polyacrylonitrile to produce water-soluble polymers of acrylic acid. This process keeps the polymer particles in a solid state, thus avoiding a viscous and difficult to handle water solution of the hydrolyzed product. The solid state is maintained by using a minimum amount of water and a water-miscible organic liquid in a sufficient quantity to maintain the polymer particles as a thin slurry. The hydrolyzed polymer thus produced remains entirely in the solid state and is readily separated from the reaction mixture by filtration. U.S. Pat. No. 2,579,451, incorporated herein by reference, discloses acid hydrolysis of polyacrylonitrile to produce a hydrolyzed product containing from about 2% to about 75% amide groups. U.S. Pat. No. 3,709,842, incorporated herein by reference, discloses an acid hydrolysis process for producing porous hydrogels of partially hydrolyzed polyacrylonitrile. U.S. Pat. No. 4,183,884, incorporated herein by reference, discloses a process for the acid hydrolysis of polyacrylonitrile to form a hydrogel that absorbs from about 30% to about 75% water by weight. U.S. Pat. No. 3,897,382, incorporated herein by reference, discloses a method for the acid hydrolysis of acrylonitrile containing polymers to form hydrogels. U.S. Pat. No. 3,864,323, incorporated herein by reference, discloses a process for the acid hydrolysis of polyacrylonitrile. U.S. Pat. No. 3,200,102, incorporated herein by reference, discloses production of hydrolyzed polyacrylonitrile containing carbonamide groups and carboxylic acid groups generally in the ratio of about 1:1 by heating polyacrylonitrile in aqueous suspension, dispersion or emulsion to relatively high temperatures, i.e., at least about 180° C., preferably under pressure and possibly in the presence of inert gases.

Another example of a polymer in accordance with the present invention is a hydrolyzed product of a fibrous protein such as, for example, fibrin, fibronectin and elastin. Such hydrolyzed fibrous protein products that may be used in the compositions of the present invention can be prepared by known methods, such as enzymatic hydrolysis with an enzyme such as elastase, pepsin and pronase and by nonenzymatic processes including, for example, acid and alkaline hydrolysis. It is believed that the hydrolysis product of these fibrous proteins is a polymer comprising polyamino acid moieties (i.e. polypeptides) and acrylamide moieties. A preferred hydrolyzed fibrous protein product is a polyamino acid/polyacrylamide copolymer. U.S. Pat. No. 4,963,656, incorporated herein by reference, discloses a process for preparing elastin hydrolyzate having a molecular weight in excess of 200,000, preferably 1,000,000 to 2,000,000, by enzymic hydrolysis with pepsin. U.S. Pat. No. 4,419,288, incorporated herein by reference, discloses a nonenzymatic process for producing soluble elastin partial hydrolyzate. This method produces a solubilized elastin hydrolyzate that retains the basic characteristics of elastin by recovering substantially all of the desmosine and isodesmosine residues that are believed to give elastin fibers their elasticity. U.S. Pat. No. 4,363,760, incorporated herein by reference discloses a nonenzymatic process for preparing soluble partially hydrolyzed elastin. The disclosure of this patent is related to the disclosure of U.S. Pat. No. 4,419,288, discussed above.

Other polymers that are useful in the compositions of the present invention include, for example, polyols such as those prepared from partial hydrolysis of polysaccharides including, but not limited to starch, cellulose and derivatives thereof including, e.g., hydroxypropyl methylcellulose, hydroxypropyl cellulose and carboxymethyl cellulose. Hydroxypropyl methylcellulose can be prepared by reacting a purified form of cellulose obtained from, e.g., cotton waste or wood pulp with sodium hydroxide solution to produce a swollen alkali cellulose which is then treated with chloromethane and propylene oxide to produce methylhydroxypropyl ethers of cellulose. The partial hydrolysis of these and other polysaccharides can be carried out by conventional processes including, e.g., alkaline or acid hydrolysis.

It will be apparent to those skilled in the art that the examples and embodiments described herein are by way of illustration and not of limitation, and that other examples and embodiments may be devised without departing from the spirit and scope of the present invention as set forth in the appended claims.

What is claimed is:

1. A method of applying a composition to a plant comprising:
coating at least a portion of a surface of said plant with a composition comprising water droplets coated with hydrated polymer gel that releases heat over a range of dropping ambient temperatures beginning at about 32° F.

2. The method of claim 1, wherein said range of dropping ambient temperatures is from at least about 32° F. to about 27° F.

3. The method of claim 1, wherein said range of dropping ambient temperatures is from at least about 32° F. to about 22° F.

4. The method of claim 1, wherein said composition is applied by spraying.

5. The method of claim 1, further comprising coating at least a portion of said plant with a composition comprising an aqueous solution of hydrated polymer gel.

6. The method of claim 5, further comprising coating at least a portion of said plant with a composition comprising a foam comprising hydrated polymer gel.

7. The method of claim 1, further comprising coating at least a portion of said plant with a composition comprising a foam comprising hydrated polymer gel.

8. The method of claim 7, wherein said foam further comprises air bubbles having a diameter in the range of from about 10 to about 100 microns.

9. The method of claim 1, wherein said hydrated polymer gel is a hydrated copolymer gel.

10. The method of claim 1, wherein said hydrated polymer gel comprises a hydrolyzed polymer.

11. The method of claim 10, wherein the hydrated polymer gel is hydrolyzed polyacrylonitrile.

12. The method of claim 10, wherein the hydrated polymer gel is a hydrolyzed fibrous protein.

13. The method of claim 11, wherein said hydrolyzed polyacrylonitrile comprises acrylic acid and acrylamide moieties.

14. The method of claim 13, wherein said hydrolyzed polyacrylonitrile is uncross-linked.

15. The method of claim 12, wherein said hydrolyzed fibrous protein contains amino acid and acrylamide moieties.

16. The method of claim 15, wherein said hydrolyzed fibrous protein is selected from the group consisting of hydrolyzed fibronectin, hydrolyzed fibrin and hydrolyzed elastin.

17. The method of claim 1, wherein said composition further comprises one or more components selected from the group consisting of micronutrients, macronutrients, pesticides, insecticides, herbicides, rodenticides, fungicides, biocides, plant growth regulators, fertilizers, microbes, soil additives, adhesion promoting-agents, surfactants and freezing point modifiers.

18. A composition comprising:
    water droplets coated with hydrated polymer gel that, when applied to at least a portion of a surface of a plant, releases heat over a range of dropping ambient temperatures beginning at about 32° F.

19. The composition of claim 18, wherein the range of dropping ambient temperatures is from at least about 32° F. to about 27° F.

20. The composition of claim 18, wherein the range of dropping ambient temperatures is from at least about 32° F. to about 22° F.

21. The composition of claim 18, wherein said hydrated polymer gel is a hydrated copolymer gel.

22. The composition of claim 18, wherein said composition further comprises one or more components selected from the group consisting of micronutrients, macronutrients, pesticides, insecticides, herbicides, rodenticides, fungicides, biocides, plant growth regulators, fertilizers, microbes, soil additives, adhesion promoting-agents, surfactants and freezing point modifiers.

23. The composition of claim 18, wherein said hydrated polymer gel comprises a hydrolyzed polymer.

24. The composition of claim 23, wherein the hydrated polymer gel is hydrolyzed polyacrylonitrile.

25. The composition of claim 24, wherein said hydrolyzed polyacrylonitrile comprises acrylic acid and acrylamide moieties.

26. The composition of claim 25, wherein said hydrolyzed polyacrylonitrile is uncross-linked.

27. The composition of claim 23, wherein the hydrated polymer gel is a hydrolyzed fibrous protein.

28. The composition of claim 27, wherein said hydrolyzed fibrous protein comprises amino acid and acrylamide moieties.

29. The composition of claim 28, wherein said hydrolyzed fibrous protein is selected from the group consisting of hydrolyzed fibronectin, hydrolyzed fibrin and hydrolyzed elastin.

* * * * *